United States Patent [19]

Ogata et al.

[11] Patent Number: 5,403,675
[45] Date of Patent: Apr. 4, 1995

[54] SULFONATED POLYMERS FOR SOLID POLYMER ELECTROLYTES

[75] Inventors: Naoya Ogata; Masahiro Rikukawa, both of Tokyo, Japan

[73] Assignee: Maxdem, Incorporated, San Dimas, Calif.

[21] Appl. No.: 45,968

[22] Filed: Apr. 9, 1993

[51] Int. Cl.$^6$ .............................................. H01M 8/10
[52] U.S. Cl. ...................................... 429/33; 429/192
[58] Field of Search .................. 429/33, 192; 252/62.2

[56] References Cited

U.S. PATENT DOCUMENTS

| | | | |
|---|---|---|---|
| 3,484,293 | 12/1969 | Hodgdon | 429/33 |
| 3,651,030 | 3/1972 | Desaulniers et al. | 429/33 X |
| 4,943,499 | 7/1990 | Casalbore-Miceli et al. | 429/192 |
| 5,102,971 | 4/1992 | Himmler et al. | 528/167 |
| 5,227,457 | 7/1993 | Marrocco et al. | 528/183 |

OTHER PUBLICATIONS

H. L. Yeager et al., "Perfluorinated Ionomer Membranes," American Chemical Society, ACS Symposium Series 180, Washington, D.C. 1982.

Wallow, T. I. et al., "In Aqua Synthesis of Water-Soluble Poly(p-phenylene) Derivatives," J. Am. Chem. Soc, 1991, 113, 7411-12 (month n/a).

Primary Examiner—Stephen Kalafut
Attorney, Agent, or Firm—Christie, Parker & Hale

[57] ABSTRACT

Sulfonated polyphenylene solid polymer electrolytes having high proton conductivity are provided, which are stable and which maintain high conductivity at temperatures of 100° C. and above. These membranes are useful as solid polymer electrolytes for fuel cells and can be operated above the boiling point of water.

12 Claims, 3 Drawing Sheets

SULFONATED POLYMERS FOR SOLID POLYMER ELECTROLYTES

FIELD OF THE INVENTION

This invention relates to stable sulfonated polyphenylene solid polymer electrolytes which have high proton conductivity characteristics. The sulfonated polyphenylene electrolytes are particularly useful in battery and fuel cell applications.

BACKGROUND OF THE INVENTION

Solid polymer electrolytes, SPE's, are ionic polymers having very high ion conductivity. As electrolytes they are useful in electrochemical systems, primarily in batteries and fuel cells. The polymeric nature of SPE's makes them much easier to handle than liquid electrolytes. The physical construction of the electrochemical cell is greatly simplified with the use of SPE's since elaborate seals and containment systems are not needed to contain corrosive liquid electrolytes. The use of SPE's in fuel cells and batteries is well established in the art.

The use of solid polymer electrolytes can greatly simplify cell design. Liquid electrolytes must be confined with a separator and contained with seals. Liquid electrolytes are highly corrosive and more readily contaminated than solid electrolytes. Fuel and oxygen will diffuse across liquid electrolytes more readily, lowering efficiency. SPE's avoid these problems and can be made thinner, thereby lowering cell resistance. Handling of SPE's is much easier than handling liquid systems, and cell construction can be simpler.

Fuel cells with SPE's promise greater energy density than liquid electrolyte cells because of low overall weight, primarily due to simpler construction and thinner cells. The first fuel cells flown in the U.S. space program used sulfonated polystyrene SPE's, and SPE cells are still a choice for space missions. (Alkaline cells are also used.)

An SPE should have the following properties: (1) high ionic conductivity, (2) zero electronic conductivity, (3) very low permeability to gases, (4) chemical stability at the operating temperature, (5) mechanical strength, (6) low sensitivity to humidity, and (7) compatibility with catalyst.

The first of these is by far the most difficult to obtain. Current SPE's must be operated at temperatures and pressures where water is a liquid; otherwise, the membrane dehydrates, and proton conductivity is drastically reduced. Although byproduct water must be removed, care must be taken not to dry out the SPE. Water management is a major difficulty of currently available SPE's. Fuel and air streams must be pre-humidified, and temperature strictly limited to avoid dehydration. These extra control systems add significant weight and cost.

It would be highly advantageous to operate SPE fuel cells above the boiling point of water. This would greatly simplify water balance. Temperatures lower than about 80° C. require active cooling with concomitant weight and cost. The key lies in development of an SPE with high proton conductivity in the absence of condensed water. The need for hydration with sulfonated polyfluorocarbon SPE's is a result of the relatively low concentration of sulfonate groups and the hydrophobic nature of the fluorocarbon backbone. The structure of perfluorosulfonated polymer membranes is such that the sulfonate groups tend to concentrate in a water rich phase, which forms a network permeating the hydrophobic fluorocarbon regions. When dehydrated, the sulfonate groups become isolated, and proton migration between groups is difficult.

There is therefore a need for SPE's which maintain high proton conductivity above the boiling point of water and in the absence of liquid water.

SUMMARY OF THE INVENTION

In accordance with practice of the present invention, a solid polymer electrolyte is provided which comprises a rigid-rod polyphenylene polymer which has been sulfonated to contain from about 1% to about 30% by weight sulfur.

Products incorporating the rigid-rod polyphenylene polymer are also provided. In one embodiment, a fuel cell is provided which includes an anode and a cathode, along with means for introduction of fuel to the anode and means for introduction of oxidant to the cathode. The sulfonated polyphenylene polymer electrolyte of the present invention provides electrolytic contact between the anode and cathode.

BRIEF DESCRIPTION OF THE DRAWINGS

These and other features, aspects, and advantages of the present invention will be more fully understood when considered with respect to the following detailed description, appended claims, and accompanying drawings, wherein:

DETAILED DESCRIPTION OF THE INVENTION

Figure 1:
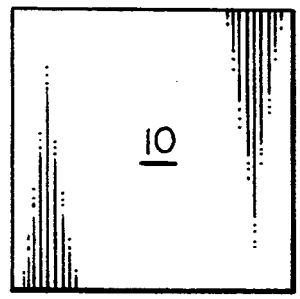
FIG. 1 is an elevation view of a sheet of film formed from a sulfonated rigid-rod polyphenylene polymer provided in accordance with practice of the present invention.

The ionic conductivity of SPE's is a function of their morphology. It is believed that SPE's have microscopic pores which contain water, and that most of the ionic groups line the surface of these pores. The bulk regions of the polymer are depleted of ionic groups. The high conductivity results from the high concentration of ionic groups in the pores along which cations may migrate and is dependent on complete interconnection of pores. It is believed that, on dehydration, these pores begin to collapse and are no longer connected, preventing the flow of ions.

We have found, surprisingly, that ionic polymers having rigid-rod polyphenylene backbones have high proton conductivity and maintain high conductivity above the boiling point of water and in the dry state. While not wishing to be bound by theory, the high proton conductivity in the absence of water may be due to the restricted motion of the sulfonate groups imposed by the rigid-rod backbone.

The rigid-rod polyphenylenes of the present invention have the general structure shown below:

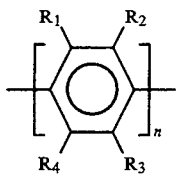

The backbone is formed of phenylene units linked primarily at the 1,4- positions. Preferably, at least 80% of the phenylene units in a rigid-rod polymer, segment, or block will have 1,4 linkages. More preferably, 90% will have 1,4 linkages. Only 1,4 linkages are depicted in the general structures shown here, for simplicity. All structures shown represent polymers with various extents of 1,4 linkages. Other linkages, including 1,2 phenylene linkages, 1,3 phenylene linkages, and all the possible naphthalene and anthracene linkages, are not shown, but implied.

The rigid-rod polymers of the present invention are linear polymers with parallel covalent bonds between the monomer units. The monomer units are not necessarily in a straight line. In some polymers, the majority of monomer units will be in a straight line (see chain A below). In other polymers, the monomer units will be staggered in a stair-like or crankshaft-like fashion (see chain B below). (The chain A and B monomer units are shown schematically without pendant organic side groups.) The monomer units can rotate about the linear axis of the covalent bonds between the monomers. However, the monomer units are restricted from flexing with respect to the bond, thus forming a rigid-rod polymer. Although the covalent bonds between the monomer units do not necessarily line up in a straight line, i.e., they may not be co-linear, the bonds are parallel, to yield a substantially linear rigid-rod polymer.

Chain A

Chain B

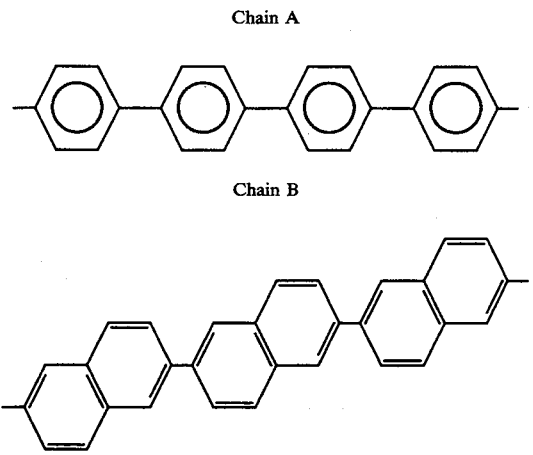

Each phenylene unit may be substituted with groups $R_1$, $R_2$, $R_3$, and $R_4$ (collectively, R). Phenylene units may have all R's equal to H; that is, no side groups other than hydrogen. The number and type of R's are chosen to retain solubility of the polymer and to adjust other properties, such as reactivity to sulfonation. Preferably, at least 50% of the phenylene monomer units will have at least one non-hydrogen solubilizing side group R. More preferably, at least 80% of the phenylene monomer units will have a solubilizing side group.

The solubilizing side groups R may be chosen from a wide variety of functional groups, including but not limited to alcohol, aldehyde, alkaryl, alkoxy, alkyl, alkyl or aryl amide, alkyl ketone, alkyl sulfide, alkylsulfonate, alkylsulfonic acid, amide, amine, aralkyl, aryl, aryl ester, arylether, aryletheretherketone, aryletherketone, arylketone, aryloxy benzoyl, aryloxy, arylsulfide, arylsulfonate, arylsulfone, arylsulfonic acid, arylsulfoxide, benzoyl, carboxylic acid, ester, fluoro or polyfluoro alkyl, fluoro or polyfluoro aryl, heteroayl, imide, imine, ketone, naphthyl, naphthoyl, phenoxybenzoyl, phenyl, sulfonamide, sulfonate, sulfone, sulfonic acid, —CHOHAr, —CHOHAr'—O—Ar, —CO$_2$Ar, —CO—Ar'—O—Ar, —OCOAr, and the like, where —Ar is an aryl group and —Ar'— is an arylene group. A given rigid-rod composition may have two or more different R groups. The R groups may also be oligomeric or polymeric, for example, but not limited to poly(phenylene oxide), poly(ether ketone), poly(ether ether ketone), poly(phenylene sulfide), poly(ethylene oxide), and the like.

Rigid-rod polyphenylene polymers and the production thereof are disclosed in International Publication No. WO91/02764, and in corresponding U.S. patent application Ser. No. 07/397,732, filed Aug. 23, 1989 and allowed Dec. 23, 1992. Publication No. WO91/02764 and application No. 07/397,732 are fully incorporated herein by this reference.

The term "solubilizing group" means a functional group which, when attached as a side chain to the polymer in question, will render it soluble in an appropriate solvent system. It is understood that various factors must be considered in choosing a solubilizing group for a particular polymer and solvent, and that, all else being the same, a larger or higher molecular weight solubilizing group will induce a higher degree of solubility. Conversely, for smaller solubilizing groups, matching the properties of the solvent and solubilizing groups is more critical, and it may be more necessary to have, in addition, other favorable interactions inherent in the structure of the polymer to aid in solubilization.

One can estimate the compatibility of a solvent and pendant organic substituent type by comparing properties, such as dielectric constant and dipole moments. There are also various types of semi-empirical sets of parameters for non-polymeric materials (such as Hildebrand's solubility parameters—J. H. Hildebrand and R. I. Scott, *The Solubility of Non-electrolytes*, 3rd Ed., Dover Publications, N.Y., 1964—and derivatives thereof) that can be used to estimate compatibility. Different sets of these solubility parameters have been developed to account for various types of solvent/solute interactions (e.g., dispersion interactions, induction, and dipole interactions), and higher solubility is achieved as more of these sets of parameters are matched. Other factors being equal, a relatively higher molecular weight pendant organic group will have a greater effect than a relatively lower molecular weight group on the solubility characteristics of the overall polymer. Therefore, it is generally preferred that the solubilizing organic groups be of moderately high molecular weight; that is, molecular weight of greater than about 300. Furthermore, when the molecular weight of the pendant organic groups is greater than about 300, they can act as the functional equivalent of the coil-like matrix of a molecular composite. Solubility can be provided, however, with pendant groups having very low molecular weight, such as phenyl groups, phenyl ketone groups, hydroxy groups, and the like.

Processes for preparing unsubstituted or alkyl substituted polyphenylenes from aryl Grignard reagents are described in T. Yamamoto et al, *Bull. Chem. Soc. Jpn.*, 1978, 51, 2091 and M. Rehahn et al, *Polymer*, 1989, 30, 1054. Paraphenylene polymers (made up of monomer units of Formula IA) can be prepared by the coupling of Grignard reagents with paraphenyl dihalides catalyzed by transition metal complexes. Thus, a mixture of 4-bromophenylmagnesium bromide (1 mole) and 4-bromo-3-alkylphenylmagnesium bromide (0.01 mole), the alkyl group having an average chain length of about 24 carbon atoms, will react in an ether solvent in the presence of a transition metal complex to yield a polyparaphenylene rigid-rod polymer having about one monomer unit per 100 monomer units substituted with a long-chain alkyl group. The transition metal-catalyzed coupling reaction proceeds selectively and quantitatively under mild conditions. In another variant of the reaction, 1,4-dibromobenzene (1.0 mole) and a 1,4-dibromobenzene substituted with a long-chain alkoxy group (0.1 mole) can be coupled in the presence of magnesium metal and a transition metal catalyst in an inert solvent, such as ether, to produce a polyparaphenylene rigid-rod polymer having, on the average, about one monomer unit out of 10 monomer units substituted with a long-chain alkoxy group. The net reaction resembles the dehalogenation polymerization of dihaloaromatic compounds with copper and sodium. Dibromo-substituted compounds are the compounds of choice for the reaction; however, in many instances, the dichloro compound can also be used if the reaction can be initiated. We have found that the $NiCl_2$ (2,2'-bipyridine) transition metal catalyst works satisfactorily for this reaction.

Coupling of the paradihaloarene monomers is preferably carried out with nickel or palladium catalysts, with zinc as the reducing agent. Such polymerizations give soluble rigid-rod polyparaphenylene polymers with high molecular weights in virtually quantitative yields. This approach has distinct advantages, since a wider variety of solvents can be employed, such as N,N-dimethylformamide (DMF), N-methylpyrrolidinone (NMP), hexamethylphosphoric triamide (HMPA), and benzene. This coupling reaction can also be used with monomers having specially reactive groups, such as nitrile and carbonyl groups. In addition, zinc is less expensive and easier to handle than magnesium.

It is highly recommended to utilize highly purified (preferably greater than about 99% pure) paradihalobenzene monomer from which any water or other aprotic impurities have been removed. For instance, a mixture of one equivalent of anhydrous nickel chloride, three equivalents of sodium iodide, seven equivalents of triphenyl phosphine, and 50 equivalents of zinc metal is effective in the polymerization of about 30 equivalents of substituted paradichlorobenzene monomer. The polymerization reaction is preferably carried out at about 50° C. but is effective from about 25° C. to about 100° C. The ratio of equivalents of monomer to equivalents of nickel catalyst can vary over the range from about 10 to about 5000, and the ratio of equivalents of zinc to equivalents of monomer is at least 1.0. The ratio of equivalents of phosphine ligands and inorganic salt promoter to equivalents of nickel catalyst varies from about 1.0 to about 10 or more.

Aryl group coupling to afford polyphenylenes has also been effected by the palladium catalyzed condensation of haloaryl boronic acids as reported by Y. H. Kim et al, *Polymer Preprints*, 1988, 29, 310 and M. Rehahn et al, *Polymer*, 1989, 30, 1060. The para-haloaryl boronic acid monomers required for formation of polyparaphenylenes can be prepared by the monolithiation of the paradihalobenzene with butyl lithium at low temperature and subsequent trimethylborate quench and aqueous acid workup. These polymerizations are carried out in aromatic and ethereal solvents in the presence of a base such as sodium carbonate. Therefore, this type of reaction is suitable for producing polyparaphenylenes substituted with organic groups such as alkyl, aryl, aralkyl, alkaryl, polyfluoroalkyl, alkoxy, polyfluoroalkoxy, and the like.

The monomer units are known or can be prepared by conventional chemical reactions from known starting materials. For example, the paradihalobenzene monomers substituted at the 2 position with an alkoxy group can be prepared from the corresponding 2,5-dihalophenol by allowing the phenol, in the presence of sodium hydroxide and benzyltriethylammonium chloride, to react with the corresponding 1-haloalkyl, such as 1-bromohexadecane.

In one embodiment of the present invention, the rigid-rod polyphenylene is a co-polymer. In another embodiment, it is a co-polymer of two or more rigid phenylene monomer units. In another embodiment, it is a co-polymer of at least one rigid phenylene monomer unit and at least one flexible monomer unit. The co-polymers may be random, block, graft, or other types known in the art. Preferably, the rigid-rod segments will have number average degree of polymerization of about 6 or greater. The following structure is a block co-polymer where —A— represents a flexible group, segment or block:

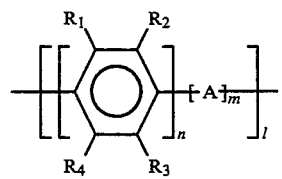

II wherein

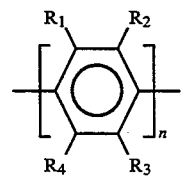

is a rigid-rod polymer segment, wherein each $R_1$, $R_2$, $R_3$, and $R_4$ on each monomer unit, independently, is H or a solubilizing side group, n and m are 1 or greater, and —[A]— is a non-rigid segment, for example, as derived from non-rigid monomers of Structure III:

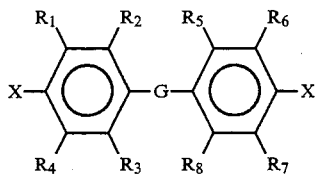     III where $R_1$–$R_8$ are independently chosen from solubilizing side groups and H, wherein G is —O—, —S—, —CH$_2$—, —CY$_2$—, —OCH$_2$—, —Oar—, —O(ArO)$_n$—, —(CH$_2$)$_n$—, —(CY$_2$)$_n$—, —CO—, —CO$_2$—, —CONY—, —O(CH$_2$CH$_2$O)$_n$—, —(CF$_2$)$_n$—, —COArCO—, —CO(CH$_2$)$_n$CO—, —C(CF$_3$)$_2$—, —C(CF$_3$)(Y)—, —NY—, —P(=O)Y—, X is Cl, or Br, or I, and Ar is an aromatic group, heteroaromatic group, or substituted aromatic group, and Y is independently selected from the group consisting of H, F, CF$_3$, alkyl, aryl, heteroaryl, or aralkyl group, and n is 1 or greater.

The following Structure IV shows a random copolymer provided in accordance with the present invention comprising of a rigid-rod phenylene of Structure I and a flexible monomer unit —A—:

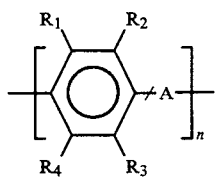     IV

In another embodiment of the present invention the rigid-rod polyphenylene will comprise rigid naphthalene or anthracene monomer units, as follows:

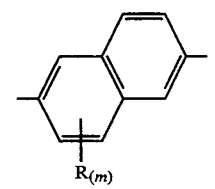     V

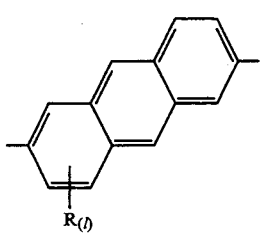     VI

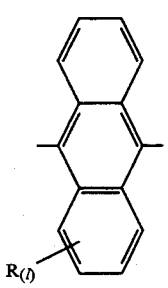     VII

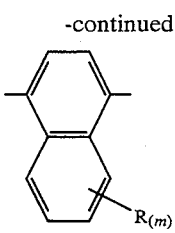     VIII

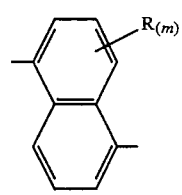     IX

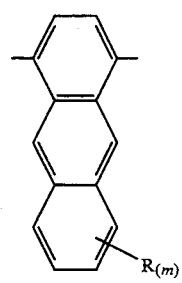     X

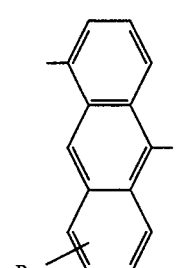     XI

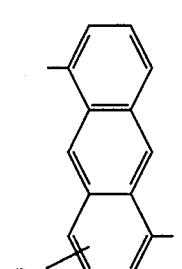     XII wherein $R_m$ and $R_l$ are R groups as defined above, with m=1 to 6 and l=1 to 8.

Any position of the naphthalene or anthracene monomer units may bear solubilizing side groups. Non-rigid-rod monomer units may also be included, with preferably less than 20%, and more preferably less than 10% of the monomer units being non-rigid-rod units. Non-rigid-rod units are defined to include naphthalene units linked in the 1,3 or 1,6 or 2,7 positions, or anthracene units linked in the 1,3 or 2,7, or other non-parallel linkages of naphthalene or anthracene units. Flexible units, segments, blocks, or grafts —A— may also be included in the rigid-rod polyphenylenes having naphthalene or anthracene units.

With the polymers of the present invention incorporating phenylene units of the Structure I, if one of the R's is benzoyl, with the other R's being hydrogen, and most of the linkages are -1,4- phenylene linkages, polymer 1 poly(benzoyl-1,4-phenylene) results. If one of the R's is 4-phenoxybenzoyl, with the other R's being hydrogen, the rigid-rod polyphenylene is poly(4-phenoxybenzoyl-1,4-phenylene) 2.

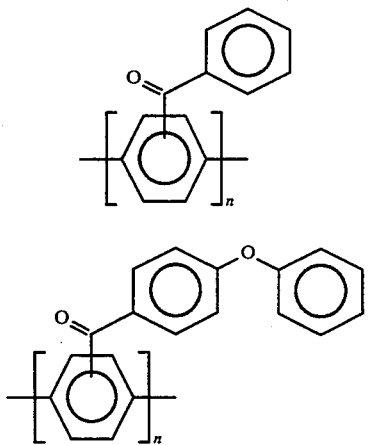

Note that the R groups benzoyl and 4-phenoxybenzoyl may be randomly distributed between the 2 and 3 positions of the phenylene units.

Because of their unusual structure rigid-rod polyphenylene polymers such as 1 and 2 have remarkable physical properties. They are the stiffest and hardest of all known isotropic thermoplastics. They have excellent chemical and thermal stability. And they are processable by both solution and thermal techniques.

Ionic groups can be introduced into polyphenylenes by sulfonation. Either the phenylene backbone or side groups or both may be sulfonated. The aromatic rings of both polymers 1 and 2 can be sulfonated using standard techniques. Exemplary, but non-limiting sulfonation methods include: treatment with concentrated sulfuric acid, treatment with fuming sulfuric acid, treatment with chlorosulfonic acid $ClSO_3H$ followed by hydrolysis, or by treatment with a mixture of sulfuric acid and thionyl chloride. The time and temperature required will depend on the particular side groups of the polyphenylene being sulfonated. In general, sulfonation conditions for a given rigid-rod polyphenylene can be determined as follows. The rigid-rod polyphenylene composition to be sulfonated (the test polymer) is first treated with concentrated sulfuric acid at room temperature for 16 hr and worked up as in Example 2 below. The resulting material is analyzed for sulfonic acid groups by titration. If the level of sulfonation is too low, the test sulfonation is repeated using more strenuous conditions roughly in the order:

| Time | Temperature | Sulfonation Agent |
|---|---|---|
| 24 hr | 25° C. | conc. sulfuric acid |
| 48 hr | 25° C. | " |
| 96 hr | 25° C. | " |
| 200 hr | 25° C. | " |
| 24 hr | 50° C. | " |
| 24 hr | 100° C. | " |
| 48 hr | 50° C. | " |
| 24 hr | 25° C. | fuming sulfuric acid |
| 24 hr | 50° C. | " |
| 48 hr | 50° C. | " |
| 24 hr | 50° C. | chlorosulfonic acid |

-continued

| Time | Temperature | Sulfonation Agent |
|---|---|---|
| 24 hr | 100° C. | " |

The test sulfonation is repeated until the desired degree of sulfonation determined by titration is reached. In some cases sensitive side groups will not withstand sulfonation conditions and an alternate route involving protection of side groups or later incorporation of sensitive side groups will be necessary. Methods for protection and further elaboration of side groups will be apparent to those skilled in the art. The degree of sulfonation may be followed by other methods as convenient, including but not limited to elemental analysis, x-ray fluorescence, secondary electron or microprobe analysis.

If the initial test sulfonation conditions result in excessive sulfonation then the reaction temperature may be lowered or reaction time decreased to reach desired levels. In general, the mildest conditions which lead to desired levels of sulfonation should be sought. For example, sulfonation of the polymer 2 in sulfuric acid at room temperature for 200 hr gives nearly the same level of sulfonation obtained after reaction for 400 hours. The phenoxy group of 2 polymer is relatively easily sulfonated. Films and membranes prepared from sulfonated polyphenylenes provided in accordance with the present invention, such as the polymers 1 and 2, have high proton conductivity.

The degree of sulfonation of the polyphenylene polymers of the present invention is preferably at least 1% by weight, i.e., the weight of sulfur in the polymer divided by the total weight of the polymer is at least 1%. At levels less than 1%, the conductivity of the polymer is less than desired. While there is no upper limit to the preferable degree of sulfonation, it is not practical to provide a polymer where the percent by weight sulfur is greater than about 30%.

The degree of sulfonation may also be defined in terms of mole percent by converting the above-described weight percent to a mole percent value. For example, in polymer 2, the molecular weight of the monomer unit is 272. Each sulfonic acid group adds a molecular weight of 80 to the monomer unit. If each monomer unit is sulfonated once (on the average), the mole percent sulfonated is 100%. The molecular weight of the sulfonated monomer unit would be 352, and the percent sulfur by weight is $32/352=9.1\%$. If each monomer unit is sulfonated twice (on the average), the mole percent sulfonation is 200%, and the percent sulfur by weight is $64/(272+2\times80)=15\%$.

While not wishing to be bound by theory the high conductivity of the rigid-rod SPE's results from the linear array of sulfonic acid groups along the backbone. Such arrangement facilitates transport of protons along the chain. The rigidity of the polymer backbone also prevents clustering of sulfonate groups and formation of isolated regions of ionic groups which would prevent ion mobility.

Solid polymer electrolytes comprising sulfonated rigid-rod polyphenylene may be homopolymers, block co-polymers with rigid-rod blocks, random co-polymers, blends, alloys, mixtures, and the like. For the purposes of this invention rigid-rod polyphenylenes are taken to be polymers which incorporate sidechain substituted or unsubstituted rigid-rod polyphenylene blocks having number average block length of about six or more, or blocks of naphthalene or anthracene monomer units having rigid-rod or crankshaft structures and number average block lengths of about six or more.

While SPE's are typically used in the form of a membrane other structures may be possible. For example, referring to FIG. 1, a sheet or film 10 of a sulfonated rigid-rod polyphenylene provided in accordance with the present invention is shown. Such a film can be provided by various film-forming techniques, including extrusion, casting, and the like.

Figure 2:
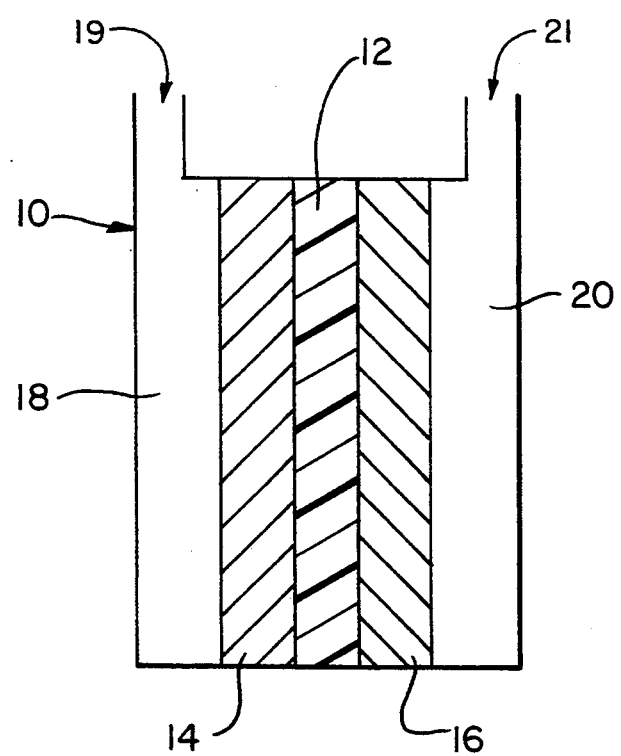
FIG. 2 is a schematic view, in partial cross-section, of a fuel cell incorporating a sulfonated rigid-rod polyphenylene polymer electrolyte provided in accordance with practice of the present invention.

For fuel cell applications the SPE is typically in intimate physical contact with the electrodes, catalyst, current collector and other supporting structure. The SPE may not have readily distinguished physical boundaries. It may be used as part of a gas diffusion electrode where gas, liquid and solid form a complex interface. The methods of construction of such electrodes and cells are well known in the art. For example, turning to FIG. 2, a schematic illustration of a fuel cell 11 incorporating a solid polymer electrolyte comprising a sulfonated rigid-rod polyphenylene 12 provided in accordance with practice of the present invention is provided. The sulfonated polyphenylene separates and provides electrolytic contact between the anode 14 and the cathode 16. Fuel is introduced into the compartment 18 via the inlet 19 for contact with the anode 14, while oxidant is introduced into the compartment 20 via the inlet 21 for contact with the cathode 16.

The sulfonated polyphenylenes of the present invention will have other applications besides fuel cells. For example, the SPE's of the present invention will be useful as battery separators, electrolytes for electrosynthesis cells, electrolytes for electrolysis cells, electrolytes for gas generating electrochemical systems, as ionic membranes in electrochemical sensors, as electrolytes in electrochemical scrubbers and other purification systems, and as electrolytes in primary and secondary batteries. In some of these applications the SPE will be used in a salt form, for example with sodium counter ions or other alkali metal cation counter ions. Other applications for the SPE's of the present invention will be apparent to one skilled in the art.

It will be understood by one skilled in the art that the exact composition of the SPE will depend on its environment. The degree of hydration will depend on the humidity and temperature. If the SPE is immersed in a liquid the composition of the liquid will determine the state of the SPE. The SPE may exchange protons, other cations, and to some extent anions with the surrounding solution. The pH of the SPE may be changed by adjusting the pH of the liquid phase in contact with the SPE. The SPE may be entirely in the acid form, meaning essentially all of the sulfonic groups are protonated. The SPE may be in the sodium form where all the sulfonic groups have sodium cations as counter ions. Other cations may be used such as cesium, potassium, lithium, calcium, magnesium, quaternary amines, or combinations of these. Transition metals and heavy metals may also be counter ions, for example where the ionic membrane is used to separate mixtures of metal salts.

It will also be apparent to one skilled in the art that the ionic polymers comprising the SPE's of the present invention may be crosslinked to various extents. Crosslinking changes the solubility and mechanical properties of the SPE. Lightly crosslinked materials will swell greatly in compatible solvents; more highly crosslinked polymers will swell less. Crosslink density may be used to optimize the ionic conductivity by controlling the amount of solvent absorption into the SPE network. Crosslinks may be formed before, during, or after sulfonation. Typically, a bifunctional reactive compound is mixed and allowed to react with the ionic polymer.

GENERAL PROCEDURES

1. 2,5-dichlorobenzoyl-containing Compounds

A wide variety of 2,5-dichlorobenzoyl-containing compounds (e.g., 2,5-dichlorobenzophenones and 2,5-dichlorobenzamides) can be readily prepared from 2,5-dichlorobenzoylchloride. Pure 2,5-dichlorobenzoylchloride is obtained by vacuum distillation of the mixture obtained from the reaction of commercially available 2,5-dichlorobenzoic acid with a slight excess of thionyl chloride in refluxing toluene. 2,5-dichlorobenzophenones (e.g., 2,5-dichlorobenzophenone, 2,5-dichloro-4'-methylbenzophenone, 2,5-dichloro-4'-methoxybenzophenone, and 2,5-dichloro-4'-phenoxybenzophenone) are prepared by the Friedel-Crafts benzoylations of an excess of benzene or substituted benzenes (e.g., toluene, anisole, or diphenyl ether, respectively) with 2,5-dichlorobenzoylchloride at 0°–5° C. using 2–3 mole equivalents of aluminum chloride as a catalyst. The solid products obtained upon quenching with water are purified by recrystallization from toluene/hexanes. 2,5-dichlorobenzoylmorpholine and 2,5-dichlorobenzoylpiperidine are prepared from the reaction of 2,5-dichlorobenzoylchloride and either morpholine or piperidine, respectively, in toluene with pyridine added to trap the hydrogen chloride that is evolved. After washing away the pyridinium salt and any excess amine, the product is crystallized from the toluene solution.

2. Activated Zinc Powder

Activated zinc powder is obtained after 2–3 washings of commercially available 325 mesh zinc dust with 1 molar hydrogen chloride in diethyl ether (anhydrous) and drying in vacuo or under inert atmosphere for several hours at about 100°–120° C. The resulting powder should be sifted (e.g., a 150 mesh sieve seems to be satisfactory), to remove the larger clumps that sometimes form, to assure high activity. This material should be used immediately or stored under an inert atmosphere away from oxygen and moisture.

EXAMPLE 1

Preparation of Poly(Benzoyl-1,4-phenylene)

Anhydrous bis(triphenylphosphine) nickel(II) chloride (34.7 g; 53 mmole), triphenylphosphine (166.6 g; 741 mmole), sodium iodide (34.6 g, 231 mmole), and 325 mesh activated zinc powder (181.8 g, 2.8 mole) are weighed into a bottle under an inert atmosphere and added to an oven dried 12-liter flash containing 1.6 liters of anhydrous N-methylpyrrolidinone (NMP), against a vigorous nitrogen counterflow. This mixture is stirred for about 15 minutes, leading to a deep red coloration. Solid 2,5-dichlorobenzophenone and another 0.8 liters of anhydrous NMP are then added to the flask. After an initial slight endotherm (due to dissolution of monomer), the temperature of the vigorously stirred reaction mixture warms to about 60° C. over 30 minutes and is held there (60°–65° C.) by use of a cooling bath. After stirring for an additional 10–15 minutes, the viscosity of the reaction mixture increases drastically, and stirring is stopped. After heating this mixture for several days at 65° C., the resulting viscous solution is poured into 10 L of 1 molar hydrochloric acid in ethanol to dissolve the excess zinc metal and to precipitate the macromonomer. This suspension is filtered and the precipitate triturated with acetone and dried to afford 283 g (85% yield) of a fine pale yellow powder.

EXAMPLE 2

Preparation of Poly(4-phenoxybenzoyl-1,4-phenylene)

2,5-Dichloro-4'-phenoxybenzophenone

To a 22 L open-mouth round bottom flask fitted with a three-necked flange head, a mechanical stirrer, a nitrogen inlet and an outlet connected to a HCl scrubbing tower, is added 2,5-dichlorobenzoic chloride (4500 g, 21.5 mol) and phenyl ether (5489 g, 32.3 mol). The solution is cooled in ice to 5° C. under stirring, and aluminum chloride (3700 g, 27.8 mol) is added slowly, over a period of about 10 minutes. The temperature of the reaction mixture is about 35° C. after the addition. The mixture is then stirred for about 30 minutes and poured into about 20 gallons of ice water. The large reddish mass is dissolved by adding about 12 L of methylene chloride and stirring. The organic layer is separated and the aqueous layer is extracted with some methylene chloride. After methylene chloride is removed from the combined organic layer by distillation, the residue is recrystallized twice from cyclohexane (2×10 L), washed with cooled hexane, air dried, and then vacuum dried, to afford 5387 g monomer (73%). The mother liquor is kept for later recovery of remaining product.

Poly(4-phenoxybenzoyl-1,4-phenylene)

To a 12 L open-mouth round bottom flask equipped with a flange head, an air driven stirrer, a thermowell with a thermocouple, and a nitrogen purge line, is added under nitrogen bis(triphenylphosphine)nickel(II) chloride (58.2 g, 88.9 mmol), sodium iodide (54.7 g, 365 mmol), triphenylphosphine (279.3 g, 1065 mmol), 325 mesh activated zinc dust (239.5 g, 3663 mmol) and anhydrous N-methylpyrrolidinone (NMP) (3400 ml). The solution is stirred and heated with a hot air gun to 40° C. The monomer 2,5-dichloro-4'-phenoxybenzophenone (935 g, 2725 mmol) is added. After about 15 minutes, the mixture becomes viscous. After 17 minutes, the solution becomes very thick, and the stirring is stopped. The reaction mixture is allowed to come to room temperature and is left to stand overnight. The next morning, the reaction mixture is coagulated into an acetone bath and ground up in a blender. The crude polymer is then stirred for several days in 1 molar hydrochloric acid in ethanol to remove the excess zinc metal. The polymer is collected by filtration, washed with water and acetone, and dissolved in 16 L of methylene chloride. The solution is filtered through 10 μm polypropylene membrane with the aid of celite, coagulated in the same volume of acetone, filtered, extracted with acetone for three days, and dried, to afford 700 g pale yellow polymer (94%).

EXAMPLE 3

Sulfonation of Poly(4-phenoxybenzoyl-1,4-phenylene)

Twenty five grams of poly(4-phenoxybenzoyl-1,4-phenylene), provided in accordance with a process such as that outlined in Example 2, was dissolved in chloroform and was reprecipitated by pouring into excess methanol. This process was repeated three times. The resulting solid was oven dried overnight at 100° C. The dry solid was pulverized by hand in a mortar and pestle. Ten grams of pulverized poly(4-phenoxybenzoyl-1,4-phenylene) was dissolved in 100 ml concentrated sulfuric acid under a nitrogen atmosphere. The solution was held at room temperature for the desired time (see figure) and then poured into a large excess of water. The precipitate was collected by filtration and washed with water. The precipitate was pulverized and washed with water until the wash water came to pH=7. The sulfonated poly(4-phenoxybenzoyl-1,4-phenylene) was then dialyzed against distilled water using a cellulose acetate membrane.

Figure 3:
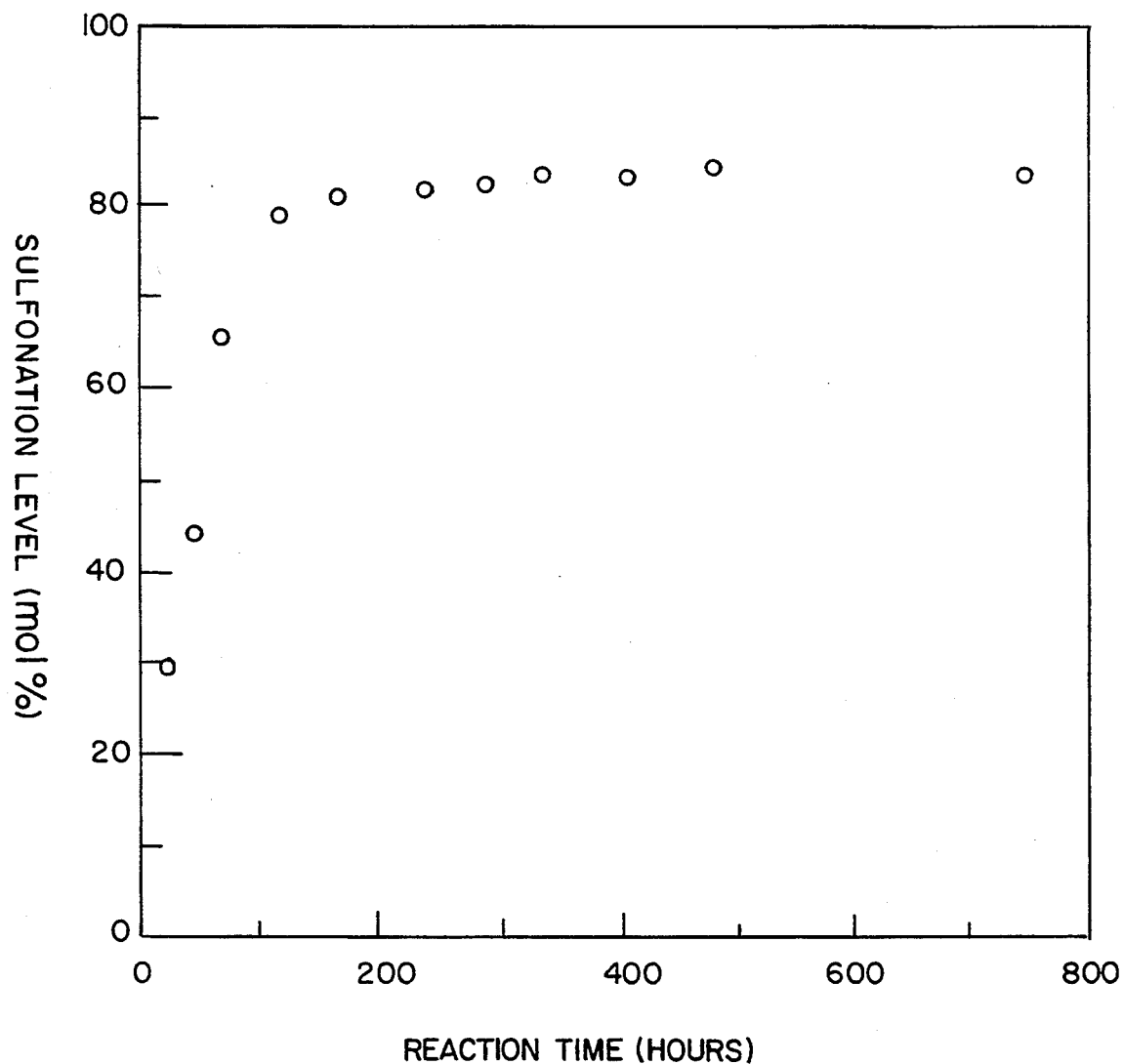
FIG. 3 is a graph of sulfonation level in mol percent as a function of reaction time (hrs) at room temperature provided by the Example 2 experiment.

The degree of sulfonation was determined by the following procedure. One gram of sulfonated polymer was placed in 1N aqueous sodium hydroxide, and the solution was kept at room temperature for 1 day. The solution was then back titrated with 1N HCl using phenolphthalein as an indicator. FIG. 3 shows the level of sulfonation (mol %) relative to the reaction time at room temperature.

EXAMPLE 4

Preparation of SPE Membranes with Sulfonated Poly(4-phenoxybenzoyl-1,4-phenylene)

A sulfonated polymer prepared in accordance with the procedure of Example 3 was dissolved in N-methylpyrrolidinone (NMP) and reprecipitated into tetrahydrofuran. The reprecipitated polymer was dried and redissolved in NMP to make a 2% by weight solution. Portions of this solution were cast onto clean glass plates and dried under a nitrogen stream at 100° C. for 10 hours. After drying, the membranes were removed from the glass support to give films with thicknesses between 10 and 20 microns. These membranes were washed with methanol to remove the last traces of NMP and dried at 100° C. under vacuum for 1 hour.

EXAMPLE 5

Measurement of Proton Conductivity of Membranes of Sulfonated Poly(4-phenoxybenzoyl-1,4-phenylene)

Casting film samples (13 mm in diameter, 10–20 μm in thickness) of sulfonated poly(4-phenoxybenzoyl-1,4-phenylene) prepared in accordance with the procedure of Example 4 were kept under the saturated vapor pressure of water at room temperature in a desiccator for 1 week prior to the measurements. The first sample had a 65.8 mol % sulfonation, while the second sample was 80 mol % sulfonated. The wet casting film samples were sandwiched between platinum electrodes for electrical contacts and packed in a sealed cell with stainless steel terminals which were in contact with the measuring system. Conductivity of the film was measured with a Yokokawa-Hewlett-Packard Model 4192A LF impedance analyzer over the frequency range 5 Hz to 13 MHz (OSC level 12 mV). The complex impedance method was used to determine conductivity.

Figure 4:
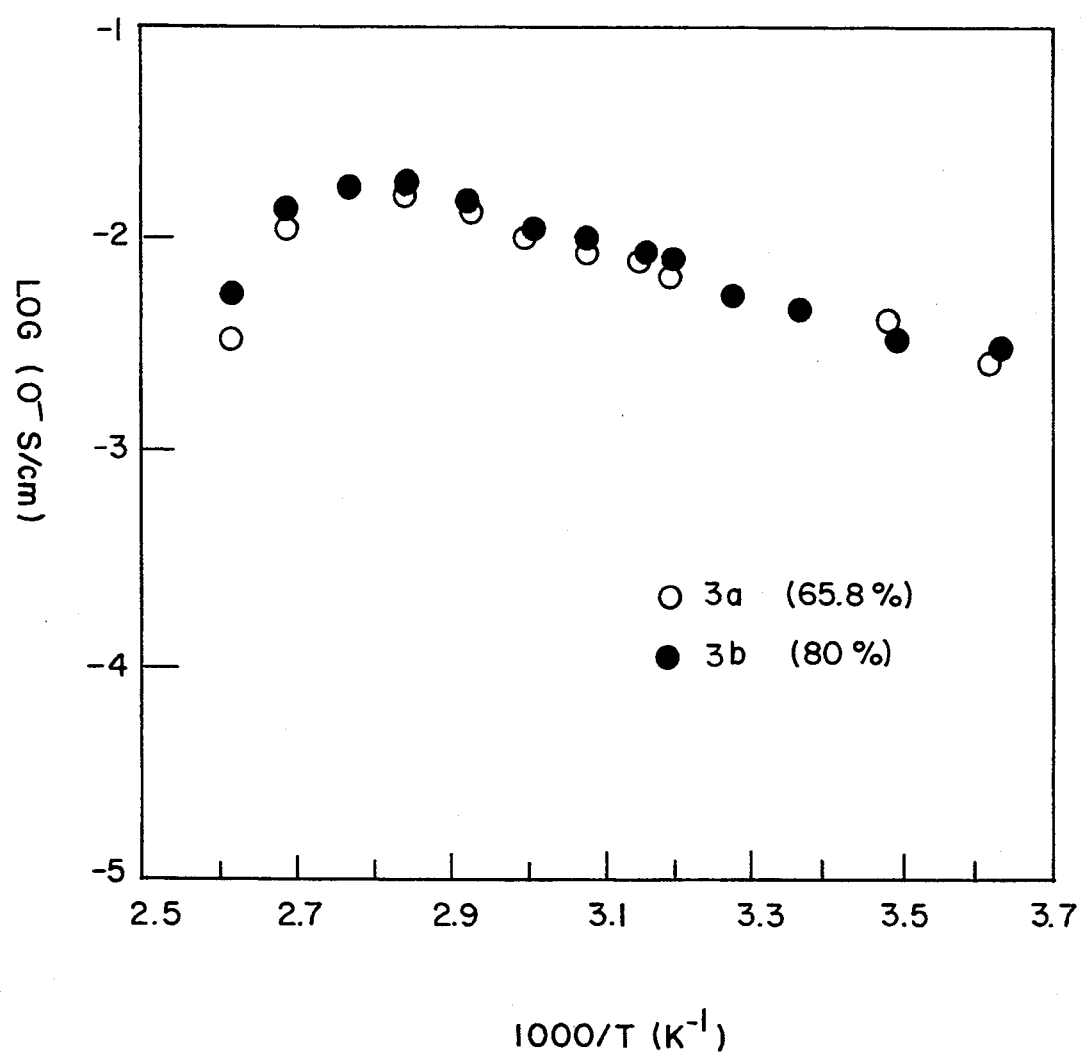
FIG. 4 is a graph showing the conductivity of sulfonated polymers having two different degrees of sulfonation.

The conductivity values as a function of temperature for two samples having different degrees of sulfonation are shown in FIG. 4. The conductivity peaks at about 0.02 S/cm at about 80° C. At 110° C. the conductivity for both samples is still above $4 \times 10^{-3}$ S/cm.

The above descriptions of exemplary embodiments of sulfonated polymers provided in accordance with the present invention are for illustrative purposes. Because of variations which will be apparent to those skilled in the art, the present invention is not intended to be limited to the particular embodiments described above.

The scope of the invention is described in the following claims.

What is claimed is:

1. An ion exchange structure comprising:
   a solid polymer electrolyte comprising a rigid-rod polyphenylene which has been sulfonated to contain from 1% to 30% by weight sulfur; and
   at least one electrode in electrical contact with the electrolyte.

2. The ion exchange structure of claim 1, wherein the rigid-rod polyphenylene has been sulfonated to 10% to 25% by weight sulfur.

3. The ion exchange structure of claim 1, wherein the sulfonated rigid-rod polyphenylene is part of a copolymer.

4. The ion exchange structure of claim 1, wherein the rigid-rod polyphenylene polymer includes solubilizing pendant groups R selected from the groups consisting of —COAr, —CHOHAr, —OAr, —COAr′—O—Ar, alkaryl, alkyl, aralkyl, aryl, and ester, where Ar is aryl and Ar′ is arylene.

5. The ion exchange structure of claim 1, wherein at least 80% of the phenylene units in the polyphenylene backbone are 1,4 linked.

6. The ion exchange structure of claim 1, wherein at least 95% of the phenylene units in the polyphenylene backbone are 1,4 linked.

7. The ion exchange structure of claim 1, wherein the rigid-rod polyphenylene has the structure:

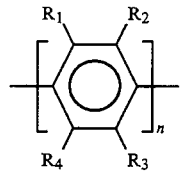

wherein $R_1$–$R_4$ are solubilizing groups or —H, and n is 6 or greater.

8. The ion exchange structure of claim 7, wherein $R_1$ is phenoxybenzoyl, and $R_2$–$R_4$ are H.

9. The ion exchange structure of claim 7, wherein $R_1$ is benzoyl, and $R_2$–$R_4$ are H.

10. The ion exchange structure of claim 7, wherein $R_1=R_2=R_3=R_4=$H on 0% to 20% of the phenylene units.

11. A fuel cell comprising an anode, a cathode, means for introduction of fuel to the anode, means for introduction of oxidant to the cathode, and a solid polymer electrolyte comprising a rigid-rod polyphenylene which has been sulfonated to contain from 1% to 30% by weight sulfur for providing electrolytic contact between the anode and cathode.

12. The ion exchange structure of claim 1 comprising an anode and a cathode in electrical contact with the electrolyte.

* * * * *